United States Patent [19]

Horwell et al.

[11] Patent Number: 5,554,644

[45] Date of Patent: Sep. 10, 1996

[54] TACHYKININ (NK$_2$) ANTAGONISTS

[75] Inventors: David C. Horwell, Foxton; William Howson, Weston Colville, both of England; Simon Osborne, Newmarket, United Kingdom

[73] Assignee: Warner-Lambert Company, Morris Plains, N.J.

[21] Appl. No.: 255,491

[22] Filed: Jun. 8, 1994

[51] Int. Cl.$^6$ .................... C07D 209/14; A61K 31/405
[52] U.S. Cl. ............................... 514/419; 548/496
[58] Field of Search ............................ 548/496; 514/419

[56] References Cited

U.S. PATENT DOCUMENTS

| | | | |
|---|---|---|---|
| 4,757,151 | 7/1988 | Horwell | 548/469 |
| 5,187,156 | 2/1993 | Matsuo et al. | 514/18 |

FOREIGN PATENT DOCUMENTS

| | | |
|---|---|---|
| 2259013 | 3/1993 | United Kingdom. |
| WO92/12140 | 7/1992 | WIPO. |
| 9219254 | 11/1992 | WIPO. |
| WO93/14084 | 7/1993 | WIPO. |

OTHER PUBLICATIONS

Nakanishi, S., *Physiological Reviews*, 1987, 67:4, 1117–1142. Month of publication not provided.
Guard, S., et al., *Neurochem Int*, 1991, 18:2, 149–165. Month of publication not provided.
Nakanishi, S., *Annu Rev Neurosci*, 1991, 14, 123–136. Month of publication not provided.
Pernow, B., *Pharmacological Reviews*, 1983, 35:2, 85–141. Month of publication not provided.
Tomczuk, B. E., et al., *Current Opinion in Therapeutic Patents*, 1991, 1:2, 197–210. Month of publication not provided.
Snider, R. M., et al., *Science*, 1991, 251, 435–437. Month of publication not provided.
Garret, C. et al., *Proc Natl Acad Sci*, 1991, 88, 10208–10212. Month of publication not provided.
Co-pending US Patent Application No. 08/131,693. Month of publication not provided.
Advenier, C., et al., *Brit J Pharmacol*, 1992, 105 (Proc Supp):77P.
Maggi, C. A. et al. *J. Auton. Pharmacol.* 13, 23–93 (1993).
Greene, T. W. et al. *Protective Groups in Organic Synthesis* (John Wiley, New York), pp. 234–243, 270, 271, 335–341 (1991).

*Primary Examiner*—Mukund J. Shah
*Assistant Examiner*—King Lit Wong
*Attorney, Agent, or Firm*—Elizabeth M. Anderson

[57] ABSTRACT

The compounds of the instant invention are ligands for the NK$_2$ receptor. The compounds are modified at the C-terminus to provide various amide isostere derivatives expected to be useful in treating obesity, anxiety, gastrointestinal ulcers, pain, stroke, and inflammation. Pharmaceutical compositions and methods of using the compounds are also included.

9 Claims, No Drawings

TACHYKININ (NK₂) ANTAGONISTS

BACKGROUND OF THE INVENTION

Over the last decade, major advances have been made in the understanding of the biology of the mammalian tachykinin neuropeptides. It is now well established that substance-P, neurokinin A (NKA), and neurokinin B (NKB), all of which share a common C-terminal sequence Phe-X-Gly-Leu-Met-NH$_2$, (Nakanishi S., *Physiol. Rev.,* 1987;67:117), are widely distributed throughout the periphery and central nervous system (CNS) where they appear to interact with at least three receptor types referred to as NK$_1$, NK$_2$, and NK$_3$, (Guard S., et al., *Neurosci, Int.,* 1991;18:149). Substance-P displays highest affinity for NK$_1$ receptors, whereas NKA and NKB bind preferentially to NK$_2$ and NK$_3$ receptors, respectively. Recently, all three receptors have been cloned and sequenced and shown to be members of the G-protein-linked "super family" of receptors (Nakanishi S., *Annu. Rev. Neurosci.,* 1991;14:123). A wealth of evidence supports the involvement of tachykinin neuropeptides in a variety of biological activities including pain transmission, vasodilation, smooth muscle contraction, bronchoconstriction, activation of the immune system (inflammatory pain), and neurogenic inflammation (Pernow B., *Pharmacol, Rev.,* 1983;35:85). However, to date, a detailed understanding of the physiological roles of tachykinin neuropeptides has been severely hampered by a lack of selective, high affinity, metabolically stable tachykinin receptor antagonists that possess both good bioavailability and CNS penetration. Although several tachykinin receptor antagonists have been described (Tomczuk B. E., et al., *Current Opinions in Therapeutic Patents,* 1991;1:197), most have been developed through the modification and/or deletion of one or more of the amino acids that comprise the endogenous mammalian tachykinins such that the resulting molecules are still peptides that possess poor pharmacokinetic properties and limited in vivo activities.

However, since 1991, a number of high-affinity nonpeptide antagonists have been reported. Snider R. M., et al., (*Science,* 1991;251:435), and Garret C., et al., (*Proc. Natl. Acad. Sci.,* 1991;88:10208), described CP-96,345 and RP 67580, respectively, as antagonists at the NK$_1$ receptor.

Advenier C., et al., (*Brit. J. Pharmacol.,* 1992;105:78), presented data on SR 48969 showing its high affinity and selectivity for NK$_2$ receptors. It is of interest that most of the nonpeptide tachykinin receptor antagonists described to date arose, either directly or indirectly, out of the screening of large compound collections using a robust radioligand binding assay as the primary screen.

Neurokinin A is widely distributed throughout the periphery and central nervous system. It is believed to mediate a variety of biological actions, via an interaction with three receptor types referred to as NK$_1$, NK$_2$, and NK$_3$, including smooth muscle contraction, pain transmission, neuronal excitation, secretion of saliva, angiogenesis, broncho-constriction, activation of the immune system and neurogenic inflammation.

Accordingly, compounds capable of antagonizing the effects of Neurokinin A at NK$_2$ receptors will be useful in treating or preventing a variety of brain disorders including pain, anxiety, panic, depression, schizophrenia, neuralgia, and addiction disorders; inflammatory diseases such as arthritis, asthma, and psoriasis; gastrointestinal disorders including colitis, Crohn's disease, irritable bowel syndrome, and satiety; allergic responses such as eczema and rhinitis; vascular disorders such as angina and migraine; neuropathological disorders including Parkinson's disease, multiple sclerosis, and Alzheimer's disease; and ophthalmic diseases including scleroderma.

The compounds of the invention, NK$_2$ receptor antagonists, are useful as anti-angiogenic agents for the treatment of conditions associated with aberrant neovascularization such as rheumatoid arthritis, atherosclerosis, and tumor cell growth. They will also be useful as agents for imaging NK$_2$ receptors in vivo in conditions such as ulcerative colitis and Crohn's disease.

SUMMARY OF THE INVENTION

This invention relates to a novel compound of formula

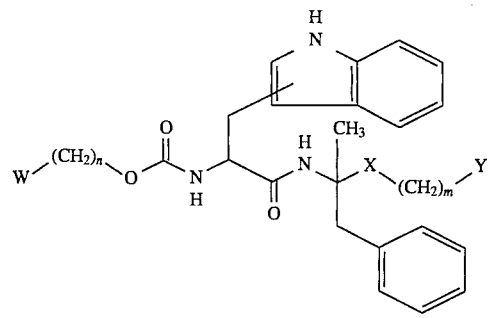

or a pharmaceutically acceptable salt thereof wherein W, n, X, m, and Y are as described below.

Preferred compounds of the invention are those of Formula I wherein

W is 1-naphthalene or 2,3-dimethoxyphenyl;

n is an integer of from 0 to 2;

X is COCH$_2$, CH(OH)CH$_2$, CH$_2$NH, or CH$_2$CH$_2$;

m is an integer of from 1 to 2; and

Y is OH, CONH$_2$, or NHSO$_2$R wherein R is CH$_3$.

More preferred compounds are those of Formula I wherein

W is 1-naphthalene or 2,3-dimethoxyphenyl;

n is 1;

X is COCH$_2$;

m is 2; and

Y is OH.

Still more preferred are:

L-Phenylalanine, N-[N-[[(2,3-dimethoxyphenyl) methoxy]carbonyl]-L-tryptophyl]-α-methyl-, 2-hydroxyethyl ester;

Carbamic acid, [2-[[1-[(2-hydroxyethoxy)methyl]-1-methyl-2-phenylethyl]amino]-1-(1H-indol-3-ylmethyl)- 2-oxoethyl]-, (2,3-dimethoxylohenyl)methyl ester, [S-(R*,R*)]-;

Carbamic acid, [2-[[2,5-dihydroxy-1-methyl- 1-(phenylmethyl)pentyl]amino]-1-(1H-indol-3-ylmethyl))- 2-oxoethyl]-, (2,3-dimethoxyphenyl)methyl ester;

Carbamic acid, [2-[[2,5-dihydroxy-1-methyl- 1-(phenylmethyl)pentyl]amino]-1-(1H-indol-3-ylmethyl)- 2-oxoethyl]-, (2,3-dimethoxyphenyl)methyl ester;

Carbamic acid, [2-[[5-hydroxy-1-methyl-2-oxo- 1-(phenylmethyl)pentyl]amino]-1-(1H-indol-3-ylmethyl)- 2-oxoethyl]-, (2,3-dimethoxyphenyl)methyl ester, [S-(R*,R*)]-; and L-Phenylalaninamide, N-[[(2,3-dimethoxyphenyl) methoxy]carbonyl]-L-tryptophyl-N-(2-hydroxyethyl)-N,α-dimethyl.

The invention also relates to a pharmaceutical composition containing an effective amount of a compound according to Formula I in combination with a pharmaceutically acceptable carrier in unit dosage form for appetite suppression. The invention also relates to a method for suppressing appetite in a mammal.

The compounds of the invention are also useful for blocking the reaction caused by withdrawal from drug or alcohol use. The compounds of the invention are also useful in reducing gastric acid secretion, in treating gastrointestinal ulcers, in treating pain, treating and/or preventing stroke, treating inflammation, and in treating anxiety.

The compounds of the invention are also useful in treating cognitive deficits, small cell lung cancer, colonic cancer, peptic ulcers, and are useful in contraception.

The invention also relates to a pharmaceutical composition for reducing gastric acid secretion containing an effective amount of a compound of Formula I in combination with a pharmaceutically acceptable carrier in unit dosage form effective for reducing gastric acid secretion.

The invention also relates to a method for reducing gastric acid secretion in mammals which comprises administering an amount effective for gastric acid secretion reduction of the composition described above to a mammal in need of such treatment.

The invention also relates to a pharmaceutical composition containing an effective amount of a compound of Formula I in combination with a pharmaceutically acceptable carrier in unit dosage form effective for reducing anxiety.

The invention also relates to a method for reducing anxiety in mammals which comprises administering an amount effective for anxiety reduction of the composition described above to a mammal in need of such treatment.

The invention also relates to a pharmaceutical composition containing an effective amount of a compound of Formula I in combination with a pharmaceutically acceptable carrier in unit dosage form effective for treating gastrointestinal ulcers.

The invention further relates to a method for treating gastrointestinal ulcers in mammals which comprises administering an amount effective for gastrointestinal ulcer treatment of the composition as described above to a mammal in need of such treatment.

The invention also relates to a pharmaceutical composition containing an effective amount of a compound of Formula I in combination with a pharmaceutically acceptable carrier in unit dosage form effective for treating inflammation.

The invention further relates to a method for treating inflammation in mammals which comprises administering an amount effective of a composition as described above to a mammal in need of such treatment.

The invention also relates to a pharmaceutical composition for preventing the withdrawal response produced by chronic treatment or abuse of drugs or alcohol.

The invention further relates to a method for treating the withdrawal response produced by withdrawal from chronic treatment or withdrawal from abuse of drugs or alcohol. Such drugs include benzodiazepines, especially diazepam, cocaine, caffeine, opioids, alcohol, and nicotine. Withdrawal symptoms are treated by administration of an effective withdrawal treating amount of a compound of the instant invention.

This invention also relates to a pharmaceutical composition containing a therapeutically effective amount of a compound according to Formula I in combination with a pharmaceutically acceptable carrier in unit dosage form for treating psychosis.

The invention also relates to a method for treating psychosis in mammals which comprises administering an amount effective for treatment of the composition described above to a mammal in need of such treatment.

This invention also relates to a pharmaceutical composition containing a therapeutically effective amount of a compound according to Formula I in combination with a pharmaceutically acceptable carrier in unit dosage form for treating asthma.

The invention also relates to a method for treating asthma in mammals which comprises administering an amount effective for treatment of the composition described above to a mammal in need of such treatment.

This invention also relates to a pharmaceutical composition containing a therapeutically effective amount of a compound according to Formula I in combination with a pharmaceutically acceptable carrier in unit dosage form for treating bladder dysfunction.

The invention also relates to a method for treating bladder dysfunction in mammals which comprises administering an amount effective for treatment of the composition described above to a mammal in need of such treatment.

This invention also relates to a pharmaceutical composition containing a therapeutically effective amount of a compound according to Formula I in combination with a pharmaceutically acceptable carrier in unit dosage form for treating arthritis and/or inflammatory pain.

The invention also relates to a method for treating arthritis and/or inflammatory pain in mammals which comprises administering an amount effective for treatment of the composition described above to a mammal in need of such treatment.

The invention further relates to methods of treating hypertension, heart failure, stroke, cognition, memory enhancement, spasticity, depression, and diabetes.

The invention further provides processes for the preparation of compounds of Formula I.

The invention further provides novel intermediates useful in the preparation of compounds of Formula I and also provides processes for the preparation of the intermediates.

The invention also relates to a pharmaceutical composition for treating pain and to a method of using a compound of Formula I for treating pain.

The invention also relates to a pharmaceutical composition for treating and/or preventing stroke and to a method of using a compound of Formula I for treating and/or preventing stroke.

The invention further relates to a process for the preparation of compounds of Formula I and to novel intermediates useful in the process.

DETAILED DESCRIPTION

The novel compounds of the instant invention are ligands for the NK$_2$ receptor. They are represented by formula

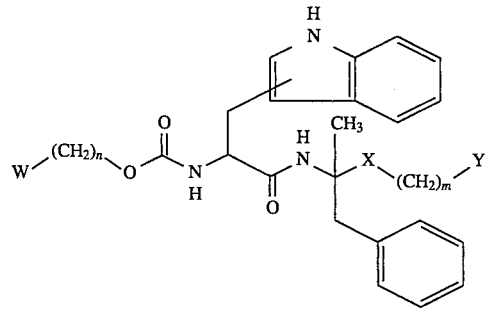

or a pharmaceutically acceptable salt thereof wherein

W is a substituted phenyl, naphthalene, or heterocycle;
n is an integer of from 0 to 3;
X is COO, $COCH_2$, $CH(OH)CH_2$, $CH_2O$, $CON(CH_3)$, $CH_2NH$, or $CH_2CH_2$;

m is an integer of from 1 to 3;
Y is OR, $CONH_2$,

NHCOR,

NHCONHR,

NHCOOR,

OCONHR, or $NHSO_2R$, wherein R is hydrogen or a straight or branched alkyl of from 1 to 4 carbons.

The compounds include solvates, hydrates, and pharmaceutically acceptable salts of the compounds of Formula I above.

The compounds of the present invention may exist as diastereomers, mixtures of diastereomers, or as the mixed or the individual optical enantiomers. The present invention contemplates all such forms of the compounds. The mixtures of diastereomers are typically obtained as a result of the reactions described more fully below. Individual diastereomers may be separated from mixtures of the diastereomers by conventional techniques such as column chromatography or repetitive recrystallizations. Individual enantiomers may be separated by conventional methods well known in the art such as conversion to a salt with an optically active compound, followed by separation by chromatography or recrystallization and reconversion to the nonsalt form.

The compounds of Formula I are capable of further forming both pharmaceutically acceptable acid addition and/or base salts. All of these forms are within the scope of the present invention.

Pharmaceutically acceptable acid addition salts of the compound of Formula I include salts derived from nontoxic inorganic acids such as hydrochloric, nitric, phosphoric, sulfuric, hydrobromic, hydroiodic, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *Journal of Pharmaceutical Science*, 66:1–19 (1977)).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali or alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine (see, for example, Berge S. M., et al., supra, 1977.

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

In the compounds of Formula I, the term "alkyl" means a straight or branched hydrocarbon radical having from 1 to 8 carbon atoms and includes, for example, methyl, ethyl, n-propyl, isopropyl, n-butyl, sec-butyl, isobutyl, tert-butyl, n-pentyl, n-hexyl, and the like except where specifically stated otherwise.

The term halogen includes fluorine, chlorine, bromine, and iodine; the more preferred halogens are fluorine and chlorine.

The term alkoxy refers to an alkyl radical attached to the remainder of the molecule by oxygen; this includes but is not limited to methoxy, ethoxy, and propoxy groups.

The phenyl, naphthyl, and heterocyclic groups may be substituted by one or more selected from alkyl such as methyl or ethyl, alkoxy such as methoxy or ethoxy, hydroxy, halogen such as fluorine, chlorine, and bromine, $NO_2$, $NH_2$, NHalkyl, $N(alkyl)_2$, and $SCH_3$.

The heterocyclic groups include but are not limited to pyridyl, 2- or 3-indolyl, benzofuranyl, furanyl, benzothienyl, and thienyl.

Some of the compounds of the invention were evaluated in tachykinin binding assays. See Table 1 below.

TABLE 1

| Compound | Binding Data |
|---|---|
| | $NK_2$ Receptor Binding $IC_{50}$ (nM) |
| IV | 150 |
| VII | >10,000 |
| XII | 250 |
| XX | 360 |
| XXI | 330 |
| XXVI | 22 |

For the $NK_2$ receptor-measurement of the binding of [$^{125}$I]-iodohistidyl neurokinin A (0.1 nM) to hamster urinary bladder membranes. See Buck and Shatzer, *Life Sci.*, 42:2701 (1988).

The data in Table 1 above shows that the compounds are $NK_2$ receptor ligands. As such they are expected to be useful in treating obesity, anxiety, gastrotestinal ulcers, pain, arthritis, inflammatory pain, stroke, inflammation, in blocking the reaction caused by withdrawal from drug or alcohol use, in reducing gastric acid secretion, in hypertension, heart failure, stroke, cognition, memory enhancement, spasticity, depression, diabetes, cancer, asthma, bladder dysfunction, and psychosis.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

For preparing suppository preparations, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

The powders and tablets preferably contain 5% to about 70% of the active component. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form preparations include solutions, suspensions, and emulsions. Sterile water or water-propylene glycol solutions of the active compounds may be mentioned as an example of liquid preparations suitable for parenteral administration. Liquid preparations can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Preferably the pharmaceutical preparation is in unit dosage form. In such form, the preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsules, cachet, or tablet itself, or it can be the appropriate number of any of these packaged forms.

The quantity of active compound in a unit dose of preparation may be varied or adjusted from 1 mg to 500 mg, preferably 5 to 100 mg according to the particular application and the potency of the active ingredient. The compositions can, if desired, also contain other compatible therapeutic agents.

In therapeutic use the mammalian dosage range for a 70-kg subject is from 1 to 1500 mg/kg of body weight per day or preferably 5 to 750 mg/kg of body weight per day optionally in divided portions. The dosages, however, per day may be varied depending upon the requirements of the patient, the severity of the condition being treated and the compound being employed. Determination of the proper dosage for a particular situation is within the skill of the art. Generally, treatment is initiated with small dosages which are less than the optimum dose of the compound. Thereafter, the dosage is increased by small increments until the optimum effect under the circumstances is reached. For convenience, the total daily dosage may be divided and administered in portions during the day if desired.

SCHEME 1

General synthesis:

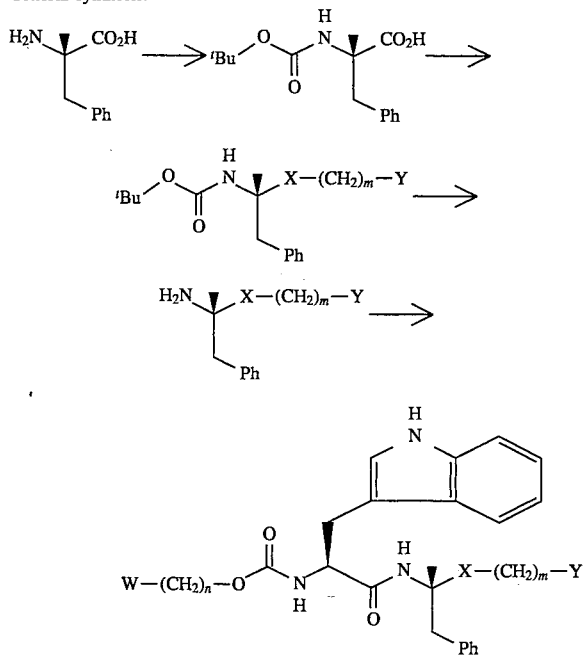

In Scheme 1 above, the α-methylphenylalanine is protected at the N-terminus by the t-butyloxycarbonyl group. Modification of the C-terminus gives various amide isostere derivatives. After removal of the t-butyloxycarbonyl group, the amine was coupled to an appropriately N-terminus protected tryptophan to give the compounds of the present invention.

SCHEME 2

Synthesis of a specific example:
A ketomethylene isostere.

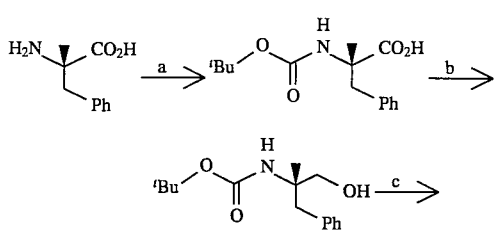

-continued
SCHEME 2

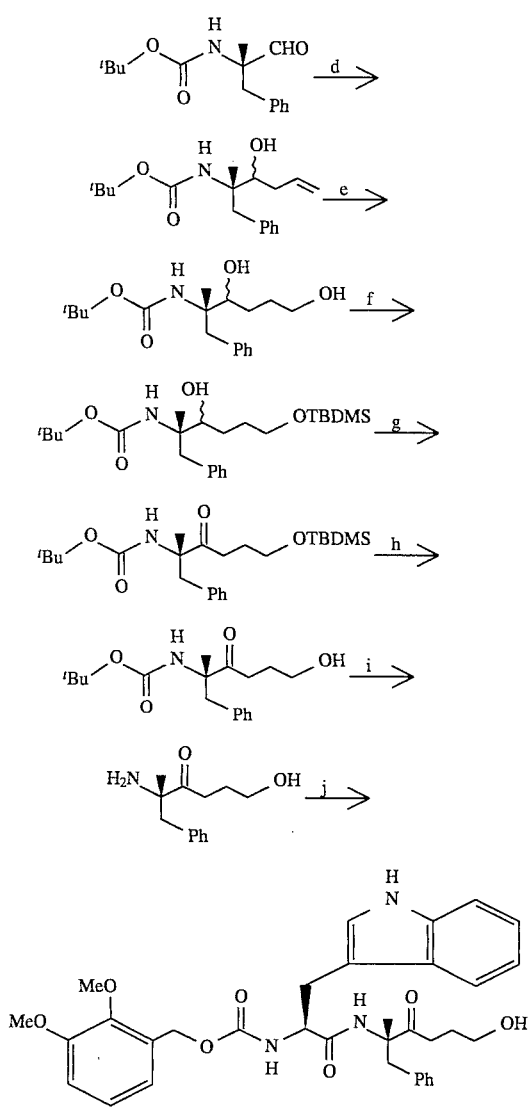

-continued
SCHEME 2

Reagents and conditions.

a) di-t-butyldicarbonate, sodium carbonate, dioxane-water, 100 hours, 23° C.;

b) ethylchloroformate, triethylamine, 1.5 hours, −30° C.; lithium borohydride, 1.5 hours, −40° C. to 0° C.;

c) TPAP, NMO, powdered molecular sieves, $CH_2Cl_2$—$CH_3CN$, 0.5 hour, 23° C.;

d) allylmagnesium bromide, THF, 2 hours, −78° C.;

e) $BH_3 \cdot THF$, 3 hours, 0° C.; $H_2O_2$, $NaHCO_3$, 1 hour, 23° C.;

f) TBDMSCl, DMAP (cat.), triethylamine, 2.5 hours, 23° C.;

g) TPAP, NMO, powdered molecular sieves, $CH_2Cl_2$—$CH_3CN$, 1.5 hours, 23° C.;

h) TBAF, THF, 0.5 hour, 23° C.;

i) TFA, $CH_2Cl_2$, 3 hours, 23° C.;

j) 2,3-Dimethoxybenzyloxycarbonyltryptophan, HBTU, iPr$_2$NEt, DMF, 19 hours, 23° C.

In Scheme 2 above a specific compound of the invention, a ketomethylene isostere is prepared.

The amino group of S-α-methylphenylalanine was protected as the t-butyloxycarbamate and the carboxylic acid functionality reduced to the alcohol via the mixed anhydride. After oxidizing to the aldehyde with TPAP, addition of allylmagnesium bromide gave a mixture of two diastereomeric alcohols. Hydroboration of the carbon-carbon double bond followed by selective protection of the primary hydroxyl and then oxidation of the secondary hydroxyl with TPAP gave one compound. Stepwise deprotection, first of the hydroxyl with TBAF, then of the amine with TFA, gave the amino alcohol which was coupled to N-(2,3-dimethoxybenzyl)oxycarbonyltryptophan using standing conditions.

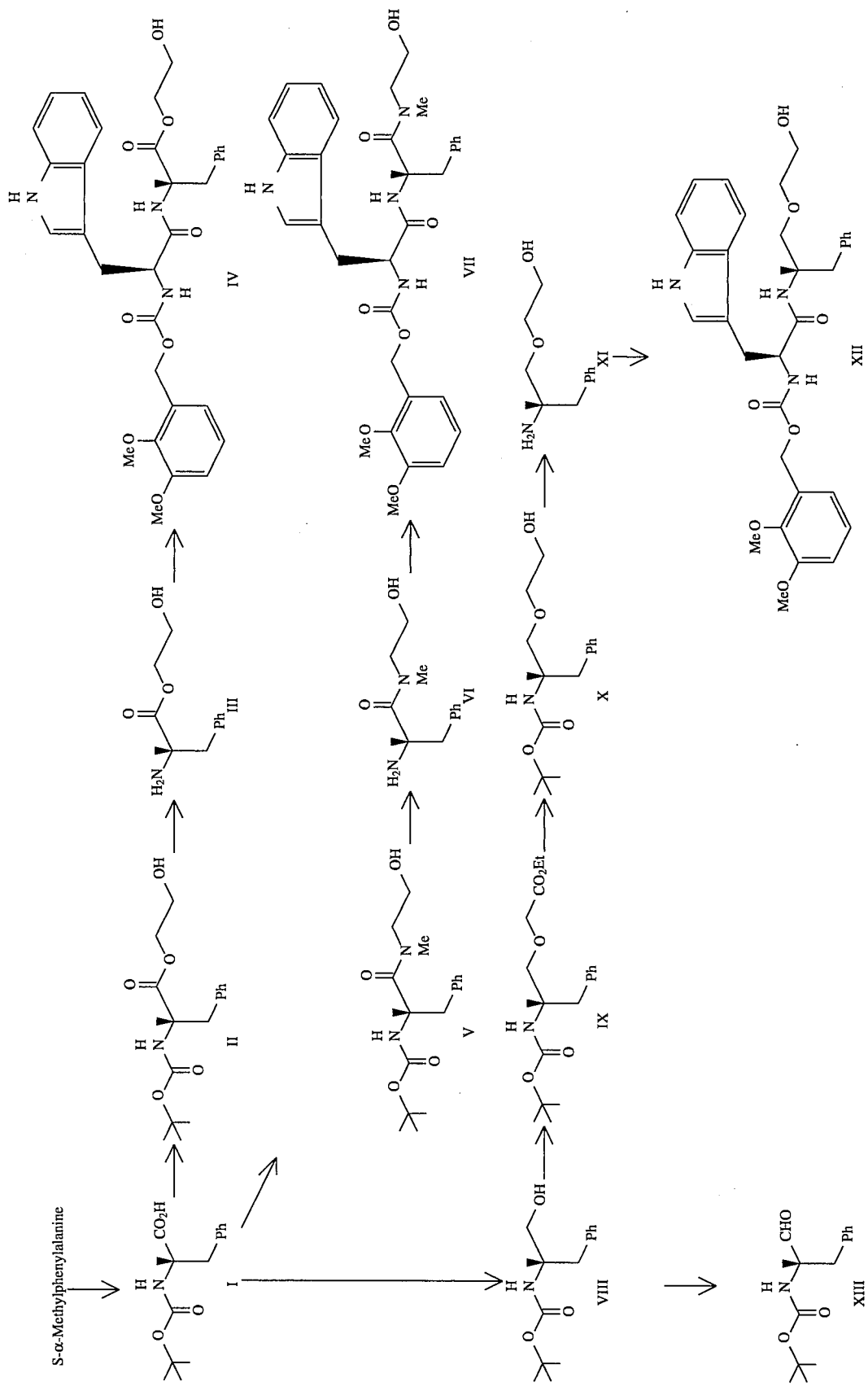

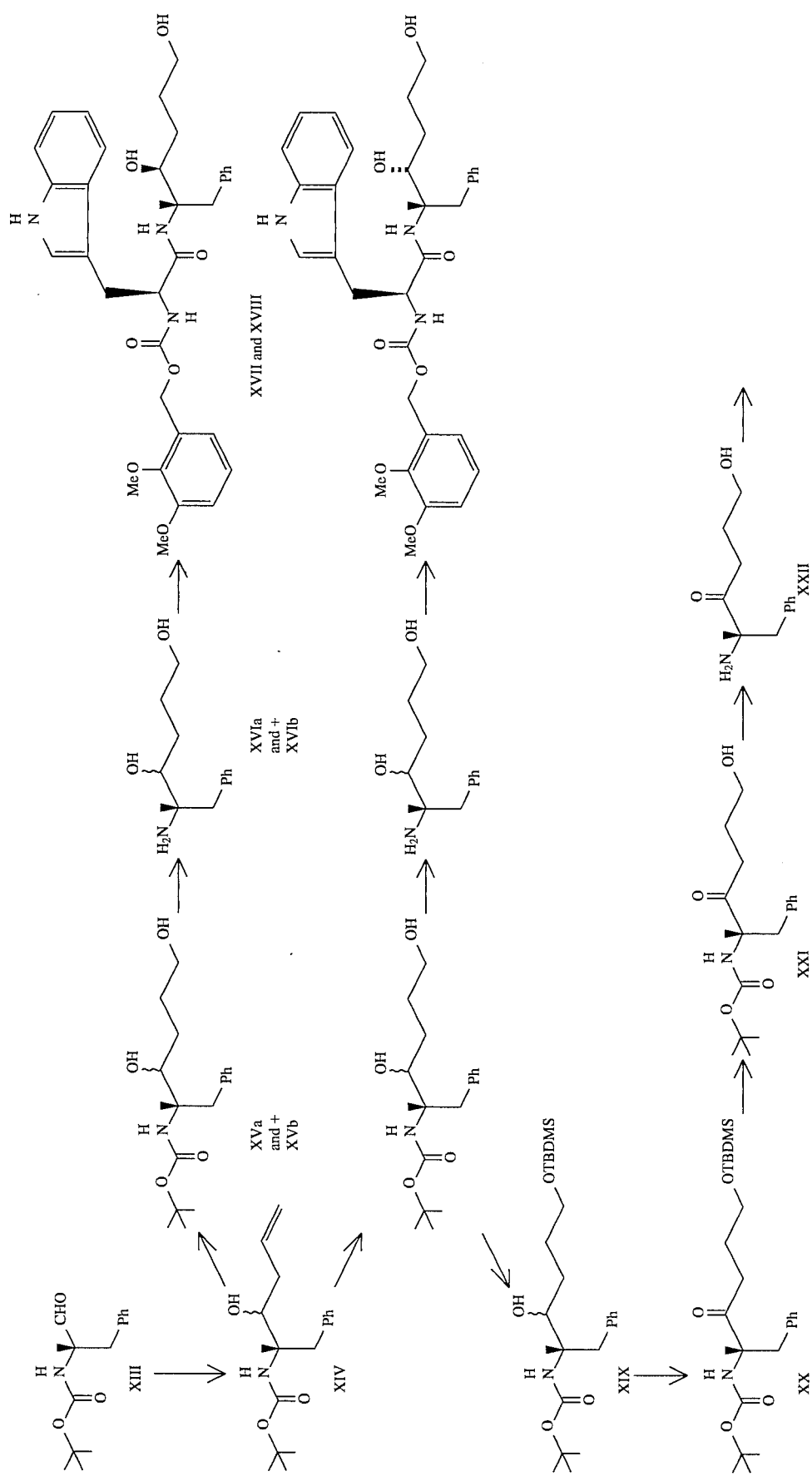
-continued
SCHEME 3

-continued
SCHEME 3
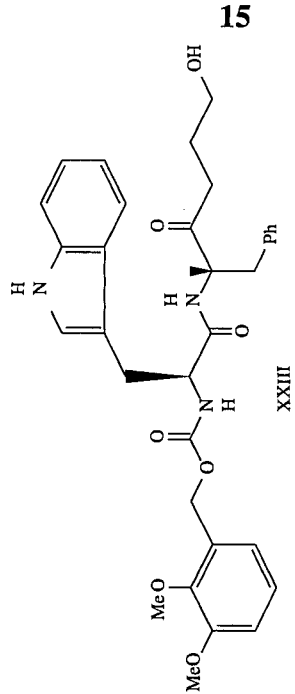

The following examples are illustrative of the instant invention. The roman numerals refer to the compounds of Scheme 3.

EXAMPLE I

To a suspension of (S)-α-methylphenylalanine (Turk J, et al., *J Org Chem* 1975;40:953) (15.0 g, 83.7 mmol) and sodium carbonate decahydrate (28.6 g, 100 mmol) in water:1,4-dioxane (120 mL:350 mL) at 0° C. was added, dropwise over 20 minutes, a solution of di-t-butyldicarbonate (27.4 g, 127 mmol) in 1,4-dioxane (60 mL). The reaction was allowed to warm to room temperature and stirred for a further 100 hours, whereupon the volatiles were removed in vacuo. After dissolving the resulting slurry in water (400 mL) and washing with diethyl ether (100 mL), the solution was acidified to pH 3.5 with 1N HCl and then extracted with $CH_2Cl_2$ (4×300 mL). Drying ($MgSO_4$) and evaporation in vacuo gave the required product I as a glassy white solid, 19.73 g, 84%. No further purification was carried out.

IR (film): $v_{max}$=3420-2900, 1715, 1660, 1500, 1450, 1400, 1370.

$^1$H NMR (300 MHz, $CDCl_3$): δ=7.30-7.00 (5H, m), 6.65 (1H, br), 3.37 (1H, d, J=14.0), 2.95 (1H, d, J=14.0), 1.40 (9H, s), 1.20 (3H, s).

EXAMPLE II

To a solution of acid I (0.431 g, 1.54 mmol) in $CH_2Cl_2$ (10 mL) at room temperature was added triphenylphosphine (0.489 g, 1.86 mmol) and ethylene glycol (0.15 mL, 2.69 mmol) followed by DEAD (0.26 mL, 1.65 mmol) dropwise. After 30 hours, the volatiles were removed in vacuo and purification by column chromatography (5:1 $CH_2Cl_2$: diethyl ether) gave the product II as an oil (0.362 g, 73%).

IR (film): $v_{max}$=3320, 2980, 1810, 1720.

$^1$H NMR (300 MHz, $CDCl_3$): δ=7.32-7.11 (5H, m), 4.86 (1H, br. s), 4.23 (2H, m), 3.79 (2H, m), 3.33 (1H, d, J=13.6), 3.15 (1H, d, J=13.6), 2.84 (1H, br. s), 1.47 (9H, s), 1.44 (3H, s).

EXAMPLE III

To a solution of II (0.362 g, 1.12 mmol) in $CH_2Cl_2$ (8 mL) at room temperature was added trifluoroacetic acid (8 mL). After 3.5 hours, the volatiles were removed in vacuo, the residue diluted with ethyl acetate (80 mL), and the solution washed with saturated sodium hydrogen carbonate solution (20 mL). After drying ($MgSO_4$) and evaporation in vacuo, the resulting crude amine III was used directly in the following step.

EXAMPLE IV

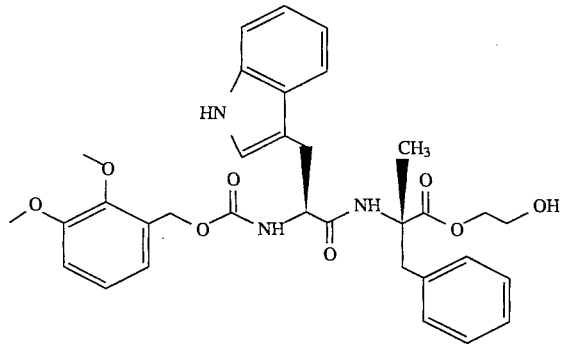

L-Phenylalanine, N-[N-[[(2,3-dimethoxyphenyl)methoxy] carbonyl]L-tryptophyl]-α-methyl-, 2-hydroxyethyl ester To a solution of N-(2,3-dimethoxybenzyl)oxycarbonyl-tryptophan (0.648 g, 1.63 mmol) in DMF (4 mL) at room temperature was added diisopropylethylamine (0.28 mL, 1.611 mmol) and HBTU (0.599 g, 1.58 mmol), whereupon the reaction turned yellow. After 15 minutes, the crude amine was added (2×2 mL DMF) and the reaction left for 23 hours. After removing the volatiles in vacuo, the residue was diluted with ethyl acetate (200 mL) and washed with saturated brine solution (20 mL), 1N HCl (20 mL), saturated sodium bicarbonate (20 mL), and saturated brine (20 mL). After drying ($MgSO_4$) and concentration in vacuo, column chromatography followed by MPLC (40% diethyl ether in $CH_2Cl_2$) gave analytically pure Compound IV, 0.100 g, 14%.

IR (film): $v_{max}$=3340, 2930, 1715, 1660.

$^1$H NMR (300 MHz, $CDCl_3$): δ=8.13 (1H, br. s), 7.70 (1H, br. s), 7.37 (1H, d, J=8.1), 7.22-6.88 (H, m), 6.74 (2H, d, J=7.2), 6.25 (1H, br. d), 5.42 (1H, br. d), 5.14 (2H, s), 4.46 (1H, br. m), 4.28 (1H, m), 4.19 (1H, m), 3.85 (3H, s), 3.80 (3H, s), 3.73 (2H, m), 3.23 (2H, t, J=7.5), 3.07 (2H, s), 1.34 (3H, s). MS m/e (CI) 604 (14) (M+H$^+$), 560 (42), 436 (58), 410 (56), 168 (100), 130 (73).

Anal. Calc. for $C_{33}H_{37}N_3O_8$: C, 66.33; H, 6.06; N, 6.82. Found: C, 68.70; H, 6.51; N, 6.68.

EXAMPLE V

To a solution of acid I (3.407 g, 12.20 mmol) in DMF (20 mL) at room temperature was added diisopropylethylamine (4.50 mL, 23.89 mmol) followed by PyBrOP (5.72 g, 12.27 mmol). After 3 minutes, N-methyl- 2-aminoethanol (2.0 mL, 24.90 mmol) was added and the reaction stirred for a further 18 hours, then quenched with water (5 mL). After removing the volatiles in vacuo, the residue was diluted with ethyl acetate (200 mL) and then washed with saturated brine (50 mL). After drying ($MgSO_4$) and evaporation in vacuo, column chromatography with 1:1 diethyl ether:$CH_2Cl_2$ and then ethyl acetate gave the product V as a white solid, 2.899 g, 71%.

IR (film): $v_{max}$=3445, 3295, 1720, 16760, 1620.

$^1$H NMR (300 MHz, $CDCl_3$): δ=7.34-7.11 (5H, m), 4.67 (1H, br. s), 3.89-3.77 (3H, m), 3.39 (1H, d, J=13.9), 3.27 (1H, br. m), 3.21 (3H, s), 3.16 (1H, d, J=13.9), 1.70 (1H, br. s), 1.47 (9H, s), 1.39 (3H, s).

EXAMPLE VI

To a solution of V (0.515 g, 1.53 mmol) in $CH_2Cl_2$ (6 mL) at room temperature was added trifluoroacetic acid (3 mL). After 2 hours, the volatiles were removed in vacuo, then the residue diluted with ethyl acetate (200 mL) and washed with saturated sodium bicarbonate solution (50 mL). After drying ($MgSO_4$) and evaporation in vacuo, the resulting crude amine VI was used directly in the following step.

EXAMPLE VII

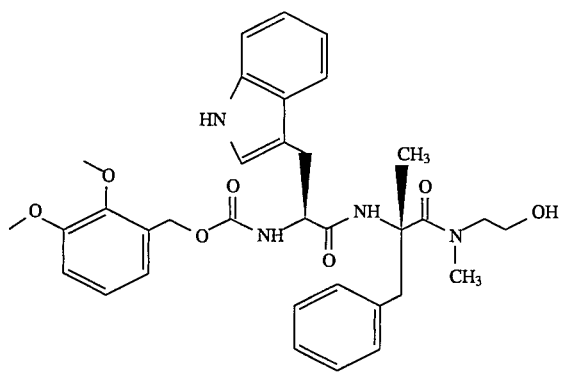

L-Phenylalaninamide, N-[[(2,3-dimethoxyphenyl)methoxy]-carbonyl]-L-tryptophyl-N-(2-hydroxyethyl)-N,α-dimethyl To a solution of N-(2,3-dimethoxybenzyl)oxycarbonyl-tryptophan (0.718 g, 1.80 mmol) in DMF (5 mL) at room temperature was added diisopropylethylamine (0.50 mL, 2.88 mmol) and HBTU (0.67 g, 1.77 mmol), whereupon the reaction turned yellow. After 3 minutes, the crude amine was added (2×2 mL DMF) and the reaction left for 8 hours. Upon quenching with water (20 mL) and diluting with ethyl acetate (200 mL), the solution was washed with saturated brine solution (40 mL), 1N HCl (40 mL), saturated sodium bicarbonate (40 mL) and saturated brine (40 mL). After drying (MgSO$_4$) and concentration in vacuo, column chromatography followed by MPLC gave 0.264 g of a white solid, not pure by analytical HPLC. Preparative HPLC (CH$_3$CN+ 0.1% TFA/H$_2$O+0.1% TFA) gave analytically pure Compound VII.

$^1$H NMR (300 MHz, CDCl$_3$) shows two rotamers (A&B) in a 1:1 mixture: δ=10.58 (2H, s, A&B), 7.62 (1H, s, A), 7.58 (1H, d, J=8.1, A), 7.52 (1H, d, J=7.8), 7.34 (1H, d, J=5.6, B), 7.32 (1H, d, J=5.9, B), 7.18-6.93 (19H, m, A&B), 6.84 (1H, m, A), 6.79 (1H, m, B), 5.01 (1H, d, J=12.5, A), 4.99 (1H, d, J=10.5, B), 4.96 (1H, d, J=10.5, B), 4.95 (1H, d, J=12.5, A), 4.74 (1H, q, J=7.1, A), 4.36 (1H, m, B), 4.01 (2H, m, A&B), 3.81 (3H, s, A), 3.80 (3H, s, A), 3.71 (3H, s, B), 3.67 (3H, s, B), 3.44 (1H, m, A), 3.39 (1H, m, B), 3.20-2.80 (18H, m, A&B), 1.28 (6H, s, A&B).

EXAMPLE VIII

To a solution of I (16.14 g, 57.8 mmol) in dry THF (140 mL) at −40° C. under nitrogen was added ethylchloroformate (8.0 mL, 83.67 mmol) followed by triethylamine (12.0 mL, 86.1 mmol) and the reaction allowed to warm to −10° C. over 1.5 hours, whereupon the resulting white precipitate was filtered off and washed with dry THF (100 mL). After recooling the reaction mixture to −15° C., a solution of lithium borohydride in THF (40 mL of a 2M solution, 80 mmol) was added and the reaction left for a further 2 hours. After warming to room temperature and quenching with water (100 mL), the emulsion was extracted with CH$_2$Cl$_2$ (3×500 mL). Drying (MgSO$_4$) and concentration in vacuo followed by purification by column chromatography (1:9 diethyl ether/CH$_2$Cl$_2$) gave the product VIII as a white powder (11.20 g, 73% ).

$[α]_{20}^D$ −44.2 (c=1.07 MeOH).

IR (film): ν$_{max}$=3270, 1680, 1560.

$^1$H NMR (300 MHz, CDCl$_3$): δ=7.32-7.17 (5H, m), 4.49 (1H, br. s), 4.11 (1H, br. s), 3.69 (2H, br. s), 3.17 (1H, d, J=13.4), 2.81 (1H, d, J=13.4), 1.46 (9H, s), 1.07 (3H, s).

Anal. Calcd. for C$_{15}$H$_{21}$NO$_3$ requires: C, 67.9%; H, 8.74%; N, 5.28%.

Found: C, 67.52%; H, 8.67%; N, 5.22%.

EXAMPLE IX

To a solution of alcohol VIII (1.846 g, 6.96 mmol) in dichloroethane (10 mL) with rhodium (II) acetate dimer (0.015 g, 0.034 mmol) under nitrogen at room temperature was added a solution of ethyl diazoacetate (1.0 mL, 9.50 mmol) in dichloromethane (9 mL) via syringe pump over a period of 6 hours. Three hours after the start of addition, further rhodium (II) acetate dimer (0.015 g, 0.034 mmol) was added, and 2 hours later a further 0.015 g, 0.034 mmol. (On each occasion the green color of the solution was observed to turn to yellow). Thirty minutes after the completion of addition, the reaction mixture was diluted with dichloromethane (200 mL), washed with saturated brine (30 mL), dried (MgSO$_4$), and concentrated in vacuo. Purification by column chromatography (CH$_2$Cl$_2$), gave the product IX as a pale yellow oil (2.123 g, 87%).

IR (film): ν$_{max}$=3370, 2980, 1750, 1710, 1500.

$^1$H NMR (300 MHz, CDCl$_3$): δ=7.30-7.18 (5H, m), 4.99 (1H, br. s), 4.21 (2H, m), 4.10 (2H, s), 3.52 (1H, d, J=8.9), 3.44 (1H, d, J=8.9), 3.14 (1H, d, J=13.3), 2.99 (1H, d, J=13.3), 1.47 (9H, s), 1.27 (3H, t, J=7.2).

EXAMPLE X

To a solution of IX (1.886 g, 5.37 mmol) in THF (35 mL) at 0° C. was added a solution of LiBH$_4$ (3 mL of a 2M solution, 6 mmol). After 40 minutes, the reaction was allowed to warm to room temperature and after 4 hours, a further 3 mL LiBH$_4$ was added. After 16 hours, the reaction was quenched with saturated ammonium chloride solution (20 mL), diluted with water (60 mL), adjusted to pH 6 with 1N HCl, and the resulting solution extracted with CH$_2$Cl$_2$ (3×100 mL). After drying (MgSO$_4$), concentration in vacuo and purification by column chromatography, the product X was obtained as a pale yellow oil (1.41 g, 85%).

IR (film): ν$_{max}$=3420, 2930, 1710, 1500.

$^1$H NMR (300 MHz, CDCl$_3$): δ=7.31-7.15 (5H, m), 4.57 (1H, br. s), 3.74 (2H, br), 3.58 (3H, m), 3.42 (1H, d, J=9.1), 3.09 (1H, d, J=13.2), 2.91 (1H, d, J=13.2), 2.09 (1H, br), 1.47 (9H, s), 1.24 (3H, s).

EXAMPLE XI

To a solution of X (1.40 g, 4.53 mmol) in CH$_2$Cl$_2$ (10 mL) at room temperature was added trifluoroacetic acid (0.5 mL). After 2 hours, a further 0.5 mL trifluoroacetic acid was added. After 16 hours, the reaction mixture was quenched with saturated sodium bicarbonate solution (20 mL) and extracted with ethyl acetate (3×50 mL). After drying (MgSO$_4$) and evaporation in vacuo, the resulting crude amine XI was used directly in the following step.

EXAMPLE XII

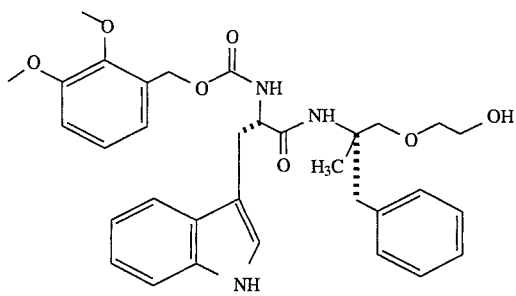

Carbamic acid, [2-[[1-[(2-hydroxyethoxy)methyl]-1-methyl- 2-phenylethyl]amino]-1-(1H-indol-3-ylmethyl)-2-oxoethyl]-, (2,3-dimethoxyphenyl)methyl ester, [S-(R*, R*)]-.

To a solution of N-(2,3-dimethoxybenzyl)oxycarbonyl-tryptophan (0.552 g, 1.39 mmol) in DMF (5 mL) at room temperature was added diisopropylethylamine (0.5 mL, 2.88 mmol) and HBTU (0.54 g, 1.42 mmol), whereupon the reaction turned yellow. After 3 minutes, the crude amine was added (2×2 mL DMF) and the reaction left for 22 hours. Upon quenching with water (10 mL) and diluting with ethyl acetate (200 mL), the solution was washed with saturated brine solution (30 mL), 1N HCl (30 mL), saturated sodium bicarbonate (30 mL), and saturated brine (30 mL). After drying (MgSO$_4$) and concentration in vacuo, column chromatography followed by MPLC (30% CH$_2$Cl$_2$ in diethyl ether to 100% diethyl ether) gave analytically pure Compound XII, 0.583 g, 48% (over two steps).
[α]$_{20}^D$=−13.4 (c=0.515 MeOH)
IR (film): vmax=3330, 2940, 1670, 1520, 1480.
$^1$H NMR (300 MHz, CDCl$_3$): δ=8.22 (1H, br. s), 7.70 (1H, br. d), 7.35 (1H, d J=8.0), 7.22-6.87 (10H, m), 5.96 (1H, br. s), 5.52 (1H, br. s), 5.18 (2H, s), 4.42 (1H, m), 3.85 (3H, s), 3.82 (3H, s), 3.57 (2H, m), 3.43 (1H, m), 3.39 (3H, m), 3.29-2.98 (4H, m) 1.16 (3H, s).

EXAMPLE XIII

To a solution of alcohol VIII (1.092 g, 4.12 mmol) in CH$_2$Cl$_2$:CH$_3$CN (150 mL:40 mL) at room temperature was added powdered molecular sieves (3.6 g), 4-methylmorpholine oxide (0.557 g, 4.74 mmol) and TPAP (0.427 g, 1.22 mmol). After stirring for 30 minutes, the reaction mixture was diluted with hexane (100 mL) and applied to the top of a hexane-silica packed column. Elution with 6:4 hexane:diethyl ether gave the desired product XIII as a white solid (0.998 g, 92%).
IR (film): v$_{max}$=3360, 1740, 1700, 1500.
$^1$H NMR (300 MHz, CDCl$_3$): δ=9.50 (1H, s), 7.32-7.08 (5H, m), 4.83 (1H, br. s), 3.20-3.09 (2H, m), 1.47 (9H, s), 1.26 (3H, s).

EXAMPLE XIV

To a solution of aldehyde XIII (2.621 g, 9.95 mmol) in THF (60 mL) under nitrogen at −15° C. was added a solution of allyl magnesium bromide (25 mL of a 1M solution in THF, 25 mmol). After 35 min the reaction was quenched with saturated ammonium chloride solution (30 mL), warmed to room temperature and diluted with water (30 mL). After adjusting to pH 6 with 1N HCl, the mixture was extracted with CH$_2$Cl$_2$ (3×150 mL), dried (MgSO$_4$), concentrated in vacuo and purified by column chromatography CH$_2$Cl$_2$) to give the product as a white solid (2.00 g, 66%).

$^1$H NMR showed the product XIV to be a 2.1:1 mixture of diastereomers. These were not separated at this point, but were used in the following reaction as a mixture.
Major isomer: $^1$H NMR (300 MHz, CDCl$_3$): δ=7.33-7.16 (5H, m), 6.05-5.90 (1H, m), 5.19-5.12 (2H, m), 4.37 (1H, br. s), 3.89 (1H, br. d), 3.28 (1H, d, J=13.5), 2.78 (1H, d, J=13.5), 2.45 (1H, m), 2.17 (1H, m), 1.45 (9H, s), 1.14 (3H, s).
Minor isomer: $^1$H NMR (300 MHz, CDCl$_3$): δ=7.29-7.19 (5H, m), 6.11-5.90 (1H, m), 5.15-5.08 (2H, m), 4.52 (1H, m), 4.45 (1H, m), 3.54 (1H, br. t, J=9.3), 3.40 (1H, d, J=13.6) 2.89 (1H, dd), 1.48 (9H, s), 1.04 (3H, s).

EXAMPLE XV

To a solution of the diastereomeric alcohols XIV (2.58 g, 8.45 mmol) in THF (10 mL) at 0° C. was added a solution of H$_3$B·THF (25 mL of a 1M solution in THF, 25 mmol). After 1 hour, a further 8 mL H$_3$B·THF was added and after 30 minutes the reaction was quenched with saturated sodium bicarbonate solution (30 mL) and 30% hydrogen peroxide (20 mL). After warming to room temperature and stirring for 20 minutes, the mixture was diluted with saturated brine (40 mL) and extracted with CH$_2$Cl$_2$ (3×100 mL). After drying (MgSO$_4$) and concentration in vacuo, purification by column chromatography (5% diethyl ether in CH$_2$Cl$_2$) gave the two diols XVIa and XVIb diastereomerically pure as white solids. Yields: minor 0.462 g; major 1.427 g total yield= 69%.
Major IR (film): v$_{max}$=3300 1680, 1560, 1170.
$^1$H NMR (CDCl$_3$): δ=7.33-7.14 (5H, m), 4.45 (1H, br. s), 3.80 (1H, d, J=10.7, 3.71 (2H, m), 3.21 (1H, d, J=13.45), 2.72 (1H, d, J=13.41), 1.83-1.78 (4H, m), 1.44 (9H, s ), 1.13 (3H, s).
Minor IR (film): v$_{max}$=3300, 1680, 1560, 1170.
$^1$H NMR (300 MHz, CDCl$_3$): δ=7.31 7.17 (5H, m), 4.39 (1H, br. s), 3.71 (2H, m), 3.48 (1H, d, J=10.3), 3.43 (1H, d, J=13.6), 2.84 (1H, d, J=13.6), 1.81 (2H, m), 1.48 (9H, s), 0.99 (3H, s).

EXAMPLE XVI (Major)

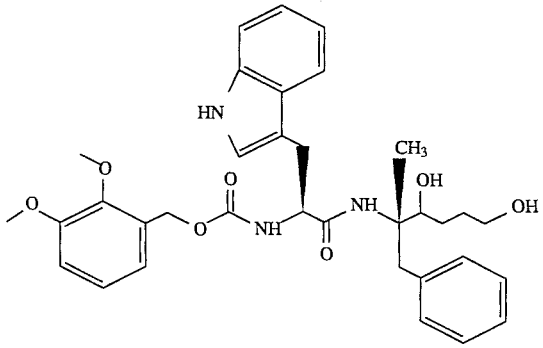

Carbamic acid, [2-[[2,5-dihydroxy-1-methyl-1-(phenylmethyl)pentyl]amino]-1-(1H-indol-3-ylmethyl)- 2-oxoethyl]-, (2,3-dimethoxyphenyl)methyl ester To a solution of XV (0.372 g, 1.15 mmol) in CH$_2$Cl$_2$ (5 mL) at room temperature was added trifluoroacetic acid (2 mL). After 2 hours, the reaction mixture was quenched with saturated sodium bicarbonate solution (30 mL) and extracted with ethyl acetate (2×60 mL). After drying (MgSO$_4$) and evaporation in vacuo, the resulting crude amine was used directly in the following step.

To a solution of N-(2,3-dimethoxybenzyl)oxycarbonyl-tryptophan (0.44 g, 1.104 mmol) in DMF (5 mL) at room temperature was added diisopropylethylamine (0.5 mL, 2.88 mmol) and HBTU (0.424 g, 1.19 mmol), whereupon the reaction turned yellow. After 5 minutes, the crude amine was added (2×3 mL DMF) and the reaction left for 15 hours. Upon quenching with water (10 mL) and diluting with ethyl acetate (200 mL), the solution was washed with saturated brine solution (40 mL), 1N HCl (40 mL), saturated sodium bicarbonate (40 mL), and saturated brine (40 mL). After drying (MgSO$_4$) and concentration in vacuo, column chromatography followed by MPLC (ethyl acetate) gave analytical pure Compound XX, 0.280 g, 40%.

$[\alpha]_{20}^D$=−49.5 (c=0.645, MeOH).

IR (film): $v_{max}$=3330, 2940, 1710, 1660.

$^1$H NMR (300 MHz, CDCl$_3$): δ=8.24 (1H, br), 7.66 (1H br. s), 7.36 (1H, d, J=8.1), 7.25-6.88 (8H, m), 6.72 (2H, d, J=7.2), 5.62 (1H, m), 5.33 (1H, br. s), 5.20 (1H, d, J=12.2), 5.15 (1H, d, J=12.2), 4.41 (1H, br. q), 3.84 (3H, s), 3.82 (3H, s), 3.69 (2H, m), 3.56 (1H, d, J=10.4), 3.27 (1H, dd, J=14.3, 5.0), 3.08 (1H, dd, J=14.4, 8.3), 2.76 (1H, d, J=13.7), 2.53 (1H, d, J=13.7), 1.69-1.57 (4H, m), 1.11 (3H, s).

Anal. Calcd. for C$_{34}$H$_{41}$N$_3$O$_7$·0.5H$_2$O: C, 66.65; H, 6.91; N, 6.86.

Found: C, 66.42; H, 6.95; N, 6.47.

EXAMPLE XVII (Minor)

Carbamic acid, [2-[[2,5-dihydroxy-1-methyl-1-(phenylmethyl)pentyl]amino]-1-(1H-indol-3-ylmethyl)- 2-oxoethyl]-, (2,3-dimethoxyphenyl)methyl ester To a solution of XV (0.253 g, 0.782 mmol) in CH$_2$Cl$_2$ (5 mL) at room temperature was added trifluoroacetic acid (2 mL). After 2.5 hours, the reaction mixture was quenched with saturated sodium bicarbonate solution (40 mL) and extracted with ethyl acetate (2×60 mL). After drying (MgSO$_4$) and evaporation in vacuo, the resulting crude amine was used directly in the following step.

To a solution of N-(2,3-dimethoxybenzyl)oxycarbonyl-tryptophan (0.345 g, 0.866 mmol) in DMF (5 mL) at room temperature was added diisopropylethylamine (0.5 mL, 2.88 mmol) and HBTU (0.34 g, 0.897 mmol), whereupon the reaction turned yellow. After 5 minutes, the crude amine was added (2×4 mL DMF) and the reaction left for 17 hours. Upon quenching with water (10 mL) and diluting with ethyl acetate (200 mL), the solution was washed with saturated brine solution (40 mL), 1N HCl (40 mL), saturated sodium bicarbonate (40 mL), and saturated brine (40 mL). After drying (MgSO$_4$) and concentration in vacuo, column chromatography followed by MPLC (ethyl acetate) gave analytically pure Compound XVIII.

IR (film): $v_{max}$=3320, 2940, 1700.

$^1$H NMR (300 MHz, CDCl$_3$): δ=8.24 (1H, br. s), 7.67 (1H, br. d, J=8.2), 7.38 (1H, d, J=9.6), 7.23-6.93 (10H, m), 5.70 (1H, br. s), 5.33 (1H, br. s), 5.18 (2H, s,), 4.52 (1H, m), 3.86 (3H, s), 3.82 (3H, s), 3.66 (2H, m), 3.59 (1H, m), 3.36 (1H, dd, J=14.5, 5.8), 3.16 (1H, dd, J=14.1, 8.0), 2.96 (2H, br. s), 1.77-1.48 (2H, m), 1.23-1.09 (2H, m), 0.85 (3H, s).

Anal. Calcd. for C$_{34}$H$_{41}$N$_3$O$_7$·0.2H$_2$O: C, 67.24; H, 6.87; N, 6.92.

Found: C, 67.63; H, 7.23; N, 6.32.

EXAMPLE XVIII

To a solution of diol XV (0.240 g, 0.742 mmol) in CH$_2$Cl$_2$ (10 mL) at room temperature was added triethylamine (0.2 mL, 1.44 mmol), DMAP (small spatula end) and TBDMSCl (0.15 g, 1.00 mmol). After stirring for 1.5 hours, the mixture was purified by column chromatography (9:1 CH$_2$Cl$_2$:diethyl ether) to give the desired product XXII as a pale yellow oil (0.25 g, 77%).

IR (film): $v_{max}$=3360, 2900, 1720, 1500.

$^1$H NMR (300 MHz, CDCl$_3$): δ=7.23-7.01 (5H, m), 4.95 (1H, br. s), 3.58 (2H, t, J=6.1) 3.17 (2H, br. s), 2.65 (2H, m), 1.76 (2H, q, J=7.2), 1.42 (9H, s), 1.29 (3H, s), 0.84 (9H, s), 0.05 (6H, s).

EXAMPLE XIX

To a solution of XIX (0.23 g, 0.53 mmol) in CH$_2$Cl$_2$:CH$_3$CN (20 mL:5 mL) at room temperature was added powdered molecular sieves (0.5 g), 4-methylmorpholine oxide (0.075 g, 0.64 mmol) and TPAP (0.05 g, 0.14 mmol). After stirring for 1.5 hours, the reaction mixture was applied to the top of a hexane/silica packed column and the product eluted off with hexane (0.5 l) followed by diethyl ether:hexane (6:4) to give the product XX as a white solid (0.193 g, 84%).

IR (film): $v_{max}$=3360, 2900, 1720, 1500.

$^1$H NMR (300 MHz, CDCl$_3$): δ=7.23-7.01 (5H, m), 4.95 (1H, br. s), 3.58 (2H, t, J=6.1), 3.17 (2H, br. s), 2.65 (2H, m), 1.76 (2H, qn, J=7.2), 1.42 (9H, s), 1.29 (3H, br. s), 0.84 (9H, s), 0.05 (6H, s).

EXAMPLE XX

To a solution of ketone XX (0.17 g, 0.39 mmol) in THF (5 mL) at room temperature was added TBAF (0.5 mL of a 1M solution in THF, 0.5 mmol), whereupon the reaction turned brown. After stirring for 25 minutes, the mixture was diluted with water (30 mL) and extracted with CH$_2$Cl$_2$ (3×30 mL). After drying (MgSO$_4$) and concentration in vacuo, purification by column chromatography (1:1 diethyl ether:CH$_2$Cl$_2$) gave the product XXI as a white solid (0.124 g, 99%).

IR (film): $v_{max}$=3350, 2980, 1710, 1500, 1170.

$^1$H NMR (300 MHz, CDCl$_3$): δ=7.23-7.20 (3H, m), 7.17-7.12 (2H, m), 4.84 (1H, br. s), 3.56 (2H, t, J=5.8), 3.14 (1H, d, J=13.7), 2.64 (2H, m), 2.11 (1H, br. s), 1.78 (2H, m), 1.37 (9H, s), 1.19 (3H, s).

EXAMPLE XXI

To a solution of XXI (0.42 g, 1.31 mmol) in CH$_2$Cl$_2$ (10 mL) at room temperature was added trifluoroacetic acid (1.5 mL). After 3 hours, the reaction mixture was quenched with saturated sodium bicarbonate solution (60 mL) and extracted with ethyl acetate (2×150 mL). After drying (MgSO$_4$) and evaporation in vacuo, the resulting crude amine XXII was used directly in the following step.

EXAMPLE XXII

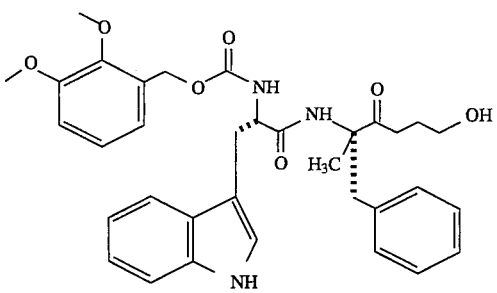

Carbamic acid, [2-[[5-hydroxy-1-methyl-2-oxo-1-(phenylmethyl)pentyl]amino]-1-(1H-indol-3-ylmethyl)-2-oxoethyl]-, (2,3-dimethoxyphenyl)methyl ester To a solution of N-(2,3-dimethoxybenzyl)oxycarbonyl-tryptophan (0.523 g, 1.31 mmol) in DMF (5 mL) at room temperature was added diisopropylethylamine (0.5 mL, 2.88 mmol) and HBTU (0.542 g, 1.49 mmol), whereupon the reaction turned yellow. After 6 minutes, the crude amine was added (2×2 mL DMF) and the reaction left for 19 hours. Upon quenching with water (10 mL) and diluting with ethyl acetate (200 mL), the solution was washed with saturated brine solution (40 mL), 1N HCl (40 mL), saturated sodium bicarbonate (40 mL) and saturated brine (40 mL). After drying (MgSO$_4$) and concentration in vacuo, column chromatography followed by MPLC (5% CH$_2$Cl$_2$ in MeOH to 10% CH$_2$Cl$_2$ in MeOH) gave analytically pure Compound XXIII, 0.305 g, 39% (over two steps).

$[\alpha]_{20}^D$=−68.2 (c=0.585, MeOH).

IR (film): $v_{max}$=3320, 2940, 1710, 1660, 1480.

$^1$H NMR (300 MHz, CDCl$_3$): δ=8.21 (1H, br. s), 7.66 (1H, br. d), 7.36 (1H, d, J=8.1), 7.24-6.99 (7H, m), 6.90 (2H, t, J=6.3), 6.69 (2H, d, J=7.37), 6.24 (1H, br. s), 5.46 (1H, br. s), 5.18 (1H, d, J=12.4), 5.14 (1H, d, J=12.4), 4.47 (1H, br.q, J=5.9), 3.85 (3H, s), 3.81 (3H, s), 3.57 (2H, m), 3.21 (2H, m), 3.02 (1H, d, J=13.8), 2.96 (1H, d, J=13.8), 2.56 (1H, dt, J=17.8, 7.1), 2.40 (1H, dt, J=17.8, 6.8), 2.09 (1H, br.s), 1.76 (2H, m), 1.21 (3H, s).

MS m/e (FAB) 602.5 (6) (M+H$^+$), 584.8 (100) (M+H$^+$−H$_2$O).

Anal. Calcd. for C$_{34}$H$_{39}$N$_3$O$_7$·0.4H$_2$O: C, 67.07; H, 6.58; N, 6.90.

Found: C, 67.06; H, 6.57; N, 6.77.

We claim:

1. A compound of formula

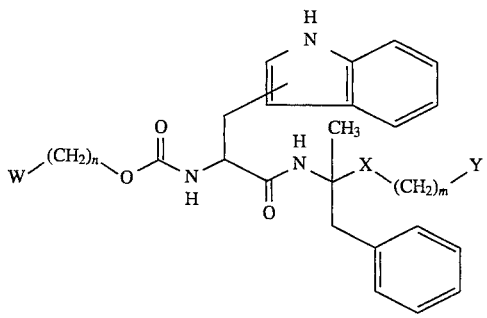

I or a pharmaceutically acceptable salt thereof wherein w is 1-naphthalene or 2,3-dimenthoxyphenyl;

n is an integer of from 0 to 2;

X is COCH$_2$, CH(OH)CH$_2$, CH$_2$NH, or CH$_2$CH$_2$;

m is an integer of from 1 to 2; and

Y is OH, CONH$_2$, or NHSO$_2$R wherein R is CH$_3$.

2. A compound according to claim 1 wherein

W is 1-naphthalene or 2,3-dimethoxyphenyl;

n is 1;

X is COCH$_2$;

m is 2; and

Y is OH.

3. A pharmaceutical composition comprising a therapeutically effective amount of a compound according to claim 1 and a pharmaceutically acceptable carrier.

4. A method of treating pain in a mammal comprising administering an effective pain treating amount of a compound according to claim 1.

5. A compound named

L-Phenylalanine, N-[N-[[(2,3-dimethoxyphenyl) methoxy]carbonyl]-L-tryptophyl]-α-methyl-, 2-hy) roxyethyl ester.

6. A compound named

Carbamic acid, [2-[[1-[(2-hydroxyethoxy)methyl]-1-methyl-2-phenylethyl]amino]-1-(1H-indol- 3-ylmethyl)-2-oxoethyl]-, (2,3-dimethoxyphenyl)methyl ester, [S-(R*,R*)]-.

7. A compound named

Carbamic acid, [2-[[2,5-dihydroxy-1-methyl- 1-(phenylmethyl)pentyl]amino]-1-(1H-indol- 3-ylmethyl)-2-oxoethyl]-, (2,3-dimethoxyphenyl)methyl ester.

8. A compound named

Carbamic acid, [2-[[5-hydroxy-1-methyl-2-oxo- 1-(phenylmethyl)pentyl]amino]-1-(1H-indol- 3-ylmethyl)-2-oxoethyl]-, (2,3-dimethoxyphenyl)methyl ester, [S-(R*,R*)]-.

9. A compound named

L-Phenylalaninamide, N-[[(2,3-dimethoxyphenyl) methoxy]carbonyl]-L-tryptophyl-N-( 2-hydroxyethyl)-N,α-dimethyl.

* * * * *